United States Patent [19]
Holt et al.

[11] Patent Number: 5,395,372
[45] Date of Patent: Mar. 7, 1995

[54] SPINAL STRUT GRAFT HOLDING STAPLE

[75] Inventors: Richard T. Holt, Louisville, Ky.; Catalina J. Carroll, Memphis, Tenn.; Robert A. Farris, Memphis, Tenn.; Troy A. McDonald, Millington, Tenn.

[73] Assignee: Danek Medical, Inc., Memphis, Tenn.

[21] Appl. No.: 117,507

[22] Filed: Sep. 7, 1993

[51] Int. Cl.⁶ ............................................ A61B 17/56
[52] U.S. Cl. ...................................... 606/61; 606/72; 606/75
[58] Field of Search .................... 606/61, 72, 74, 75, 606/219; 411/457

[56] References Cited

U.S. PATENT DOCUMENTS

| | | | |
|---|---|---|---|
| 2,952,254 | 9/1960 | Keating | 606/75 |
| 3,741,205 | 6/1973 | Markolf et al. | 606/61 |
| 4,289,123 | 9/1981 | Dunn . | |
| 4,444,181 | 4/1984 | Wevers et al. | 606/75 |
| 4,570,623 | 2/1986 | Ellison et al. | 606/75 |
| 4,611,581 | 9/1986 | Steffee . | |
| 4,787,387 | 11/1988 | Burbank, III et al. | 411/457 |
| 5,089,009 | 2/1992 | Green | 411/457 |
| 5,108,395 | 4/1992 | Laurain | 606/61 |
| 5,147,361 | 9/1992 | Ojima et al. | 606/61 |

OTHER PUBLICATIONS

"Anterior Spinal Fixation After Lumbar Corpectomy", by Thomas A. Zdeblick, M. D. et al., *The Journal of Bone and Joint Surgery*, Incorporated, vol. 73-A, No. 4, Apr. 1991, pp. 527-534.
"The Syracuse T-Plate", pp. 339-402, Spinal Instrumentation by Howard S. An and Jerome M. Cotler, © 1992 Williams & Wilkins.
"The Syracuse I-Plate", by Bayley et al., *Spine*, vol. 16, No. 3 Supplement, 1991, pp. 120-124.
"The IVBF Dual-Blade Plate and Its Application", *Spine*, by Roo et al., vol. 16, No. 3 Supplement, 1991, pp. 112-119.
"CASF Contoured Anterior Spinal Fixation System", AcroMed Corporation Catalog A 7-90, p. B-8.
Amset ALPS literature © 1991 AMS, "Innovation in Spine".
"Stafix Plate System", two page literature by Daruma.
"Kaneda Anterior Spinal Instrumentation System", AcroMed Corporation Catalog A 7-90, pp. B-9 through B-14.
"Kaneda Anterior Spinal Instrumentation for the Thoracic and Lumbar Spine" by Kiyoshi Kaneda, pp. 413-422 in *Spinal Instrumentation* by Howard S. An and Jerome M. Cotler, © 1992 Williams & Wilkins.
Zimmer Spinal Product Systems Catalog, pp. 30-33, "DUNN Anterior Spinal System" Synthes Spine, *Update* Bulletin No.: S91-2, Jul. 1, 1991.

*Primary Examiner*—Stephen C. Pellegrino
*Assistant Examiner*—Gary Jackson
*Attorney, Agent, or Firm*—Woodard, Emhardt, Naughton Moriarty & McNett

[57] ABSTRACT

A device for holding in compression, a bone graft placed in the space between two vertebral bodies and from which a diseased or injured vertebral body has been removed, comprises an elongate space-spanning plate of implant grade material having a concavo-convex cross section, with an integral prong at each end to be driven into the vertebral bodies. Each prong has a proximal portion and a distal portion, with each portion having an inboard surface facing an inboard surface of the other prong, the inboard surfaces converging as they extend from the distal ends of the prongs toward the concave surface of the plate to urge the vertebral bodies toward each other as the prongs are driven into them. The outboard surface at the proximal portion of the prong is parallel to the inboard surface and at the distal portion converges from the proximal portion to intersection with the inboard surface at the distal end of the prong. The plate has two holes in it adjacent each end for reception of bone screws but which are used during installation of the staple for reception of the locating posts of an impactor tool to properly position the tool for striking it with a mallet to drive the staple prongs into the vertebra. Consequently, as the staple is installed by striking the impactor, the prongs enter and become embedded and are anchored in the vertebral bodies adjacent the graft and urge the bodies toward each other, placing the graft under compression. Then bone screws are installed through the plate into the vertebral bodies to permanently anchor the plate and immobilize the two vertebral bodies relative to each other.

17 Claims, 5 Drawing Sheets

5,395,372

SPINAL STRUT GRAFT HOLDING STAPLE

BACKGROUND OF THE INVENTION

1. Field of the Invention

This invention relates generally to spinal surgery and more particularly to a device to hold a strut graft in compression between two vertebral bodies, for a single-level vertebrectomy.

2. Description of the Prior Art

There are instances when, as a result of injury or disease, it is necessary to remove a vertebral body. This is usually followed by the installation of an insert of natural or artificial "bone" to be fused or grafted in the place of the removed vertebra. It is necessary for the spine to be stabilized at this location.

Several patents disclose devices for holding two vertebral bodies in place after the removal of one which was between them. Examples are shown in U.S. Pat. Nos. 5,147,361 to Ojima, et al., 5,108,395 to Laurain, 4,289,123 to Dunn and 3,741,205 to Markolf et al. The Ojima patent does not appear to provide means to establish compression in the bone graft. The Laurain patent appears to require slight hypercorrection of the kyphosis followed by slight release after the graft is inserted, to "impact the graft thoroughly." The Dunn patent uses threaded adjustment rods. The Markolf patent uses integral pins at the ends of the fixation plate, but does not appear to use any specific means to hold a graft in compression. It is an object of the present invention to provide a relatively compact but sturdy device and convenient method for stabilizing and immobilizing the spinal column adjacent the site of a vertebrectomy, and compressing the graft for the fusion process.

SUMMARY OF THE INVENTION

Described briefly, according to a typical embodiment of the present invention, a staple for holding in compression a strut graft between two vertebral bodies, comprises an elongate plate of implant grade material having a concavo-convex cross section, with an integral prong at each end. Each prong has a proximal portion and a distal portion. Each of the prongs has an inboard surface facing an inboard surface of the other prong, the inboard surfaces converging as they extend from the distal ends of the prongs toward the concave surface of the plate. The inboard surface of each prong extends at an angle from the proximal end of the prong to the distal end of the prong and which is five degrees to nine degrees outward from a line normal to the concave face of the plate. Each prong has an outboard surface which, at the proximal portion of the prong is parallel to the inboard surface and, at the distal portion, converges from the proximal portion to intersection with the inboard surface at the distal end of the prong. The plate has two holes in it adjacent each end for reception of bone screws but which are used during installation of the staple for reception of the locating pins of an impactor tool to properly position the tool for striking it with a mallet to drive the staple prongs into the vertebra. Consequently, as the staple is installed by striking the impactor, the prongs enter and become embedded and are anchored in the vertebral bodies adjacent the graft and urge the bodies toward each other, placing the graft under compression. Then bone screws are installed through the plate into the vertebral bodies to permanently anchor the plate and immobilize the two vertebral bodies relative to each other.

DESCRIPTION OF THE PREFERRED EMBODIMENT

Figure 1:
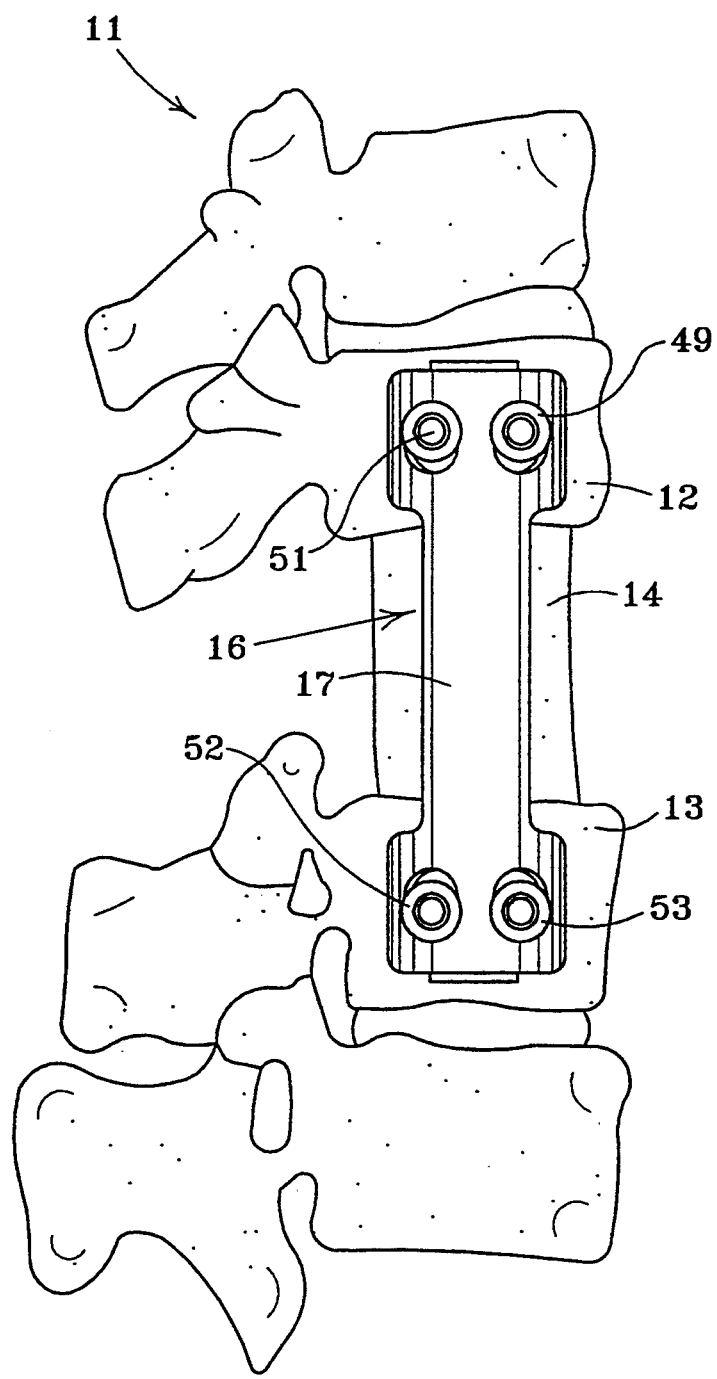
FIG. 1 is a schematic illustration of a portion of a spinal column from which one of the vertebral bodies has been removed, a bone graft has been installed, and the staple of the present invention has been installed.
Figure 2:
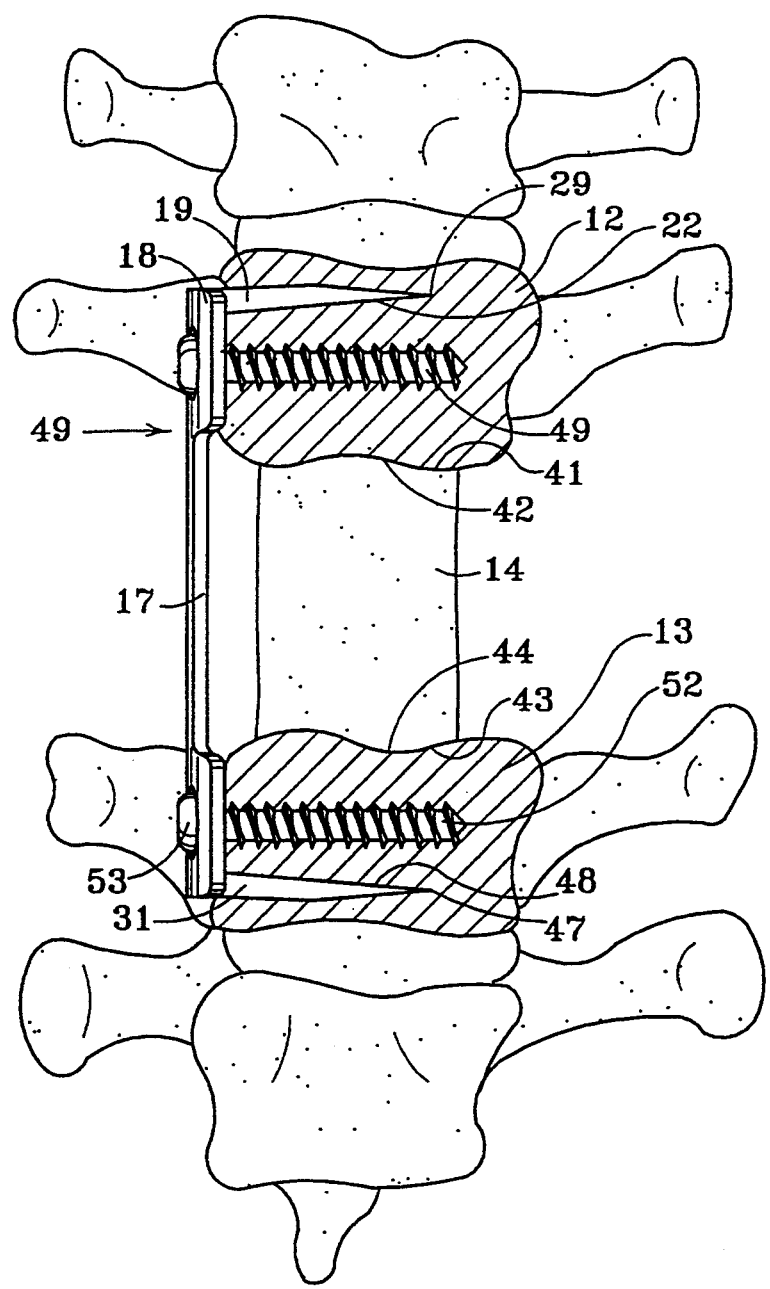
FIG. 2 is an anterior view of that portion of the spinal column as shown in FIG. 1 but with the vertebral bodies to which the strut is anchored,, shown in section.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, a portion of the spinal column is shown at 11. A single-level vertebrectomy has been performed between the thoracolumbar vertical bodies 12 and 13. A strut graft of bone 14 has been installed between the bodies 12 and 13 and placed in compression by the installation of the staple 16 according to the present invention.

Figure 3:
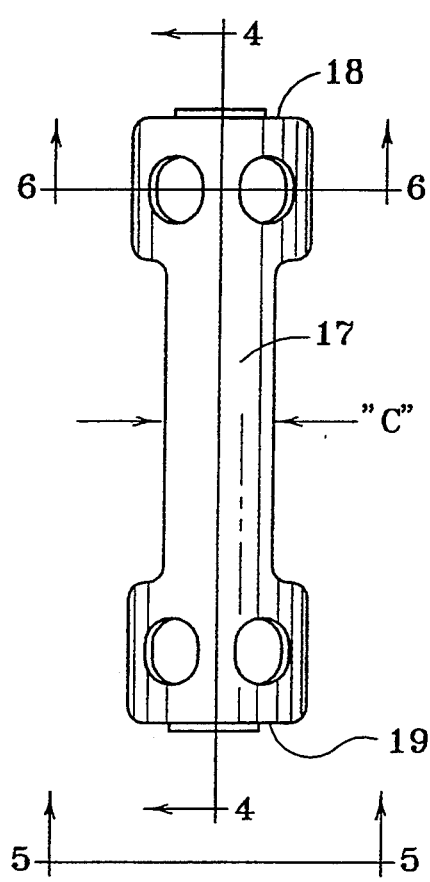
FIG. 3 is a view of the strut itself in the same orientation as FIG. 1.
Figure 4:
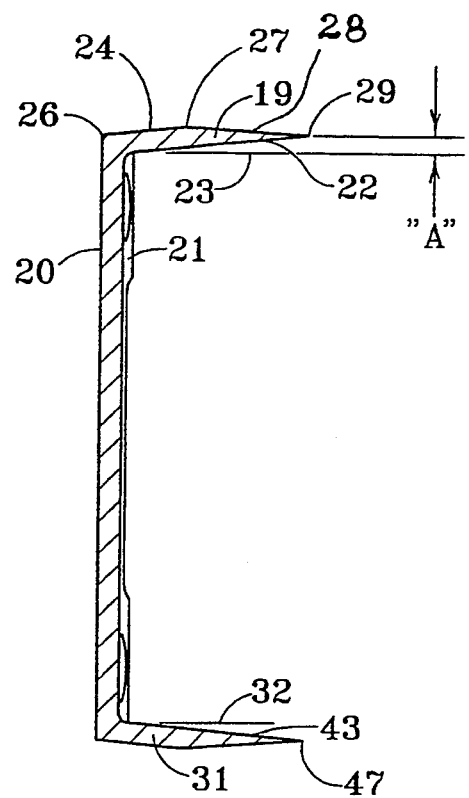
FIG. 4 is a section therethrough taken at line 4—4 in FIG. 3 and viewed in the direction of the arrows.

The staple includes the plate 17 which, as shown in FIG. 3 is symmetrical with respect to the longitudinal plane 4—4 and with respect to a transverse plane equidistant from the ends 18 and 19. Therefore, description of one end will suffice for both.

At the end 18, there is a prong 19 which projects inwardly from the convex outer 20 and concave inner face 21 (FIG. 6) of the plate. The prong has an inboard (with respect to the plate and the other prong) face 22 which projects outwardly with respect to a line 23 perpendicular to the longitudinal axis (in plane 4—4) of the plate. This surface 22 is at an angle "A" which is from 2° to 7°, preferably 5°. The prong has a two portion outboard face, the proximal portion 24 from point 26 to point 27 being parallel to the face 22. The distal portion 28 of the outer face of the prong converges from point 27 to the tip 29 where it meets face 22. While the prong 19 projects upwardly with respect to a line 23 normal to the axis of the plate as the prong projects outwardly, the lower prong 31 projects downwardly as it projects outwardly with respect to a line 32 normal to the axis of the plate at the lower end. As will be seen, this feature contributes to the compression of the strut graft bone when the staple is installed.

Figure 5:
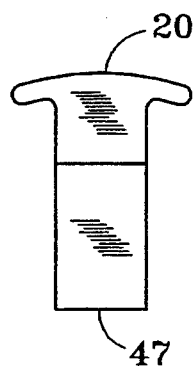
FIG. 5 shows an end thereof taken at line 5—5 in FIG. 3 and viewed in the direction of the arrows.
Figure 6:
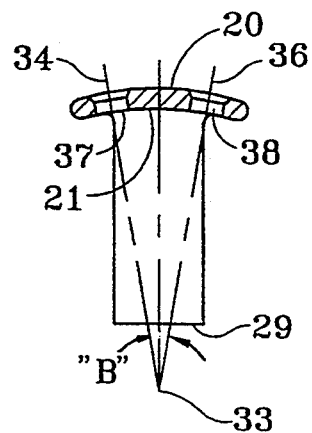
FIG. 6 is a section therethrough taken at line 6—6 in FIG. 3 and viewed in the direction of the arrows.

Referring now to FIGS. 5 and 6, the typical thickness of the plate material is 0.137 inches. It is curved about a point 33 at the intersection of the axes 34 and 36 of the two bone screw holes 37 and 38. The outside surface is curved similarly, so that the typical thickness of the plate is 0.137 inches, as is the thickness of the prongs at the proximal portions 24. The included angle between the axes 34 and 36 (angle "B" in FIG. 6) is 15.6° to 19.6°. The radius of curvature of the concave face 21 is about 1.60 inches. The overall width of the plate adjacent the ends is about 1.0 inches, while the width in the central portion ("C" in FIG. 3) is about 0.592 inches. The two bone screw holes are slightly elongate in the longitudinal direction of the plate. The material is implant-grade titanium 6AL-4V alloy. The overall length of the plate from end to end will be chosen based upon the site of use, and may range from 2.165 inches to 3.543 inches. The length of the prong from the convex face of the plate is 1.32 inches.

Figure 7:
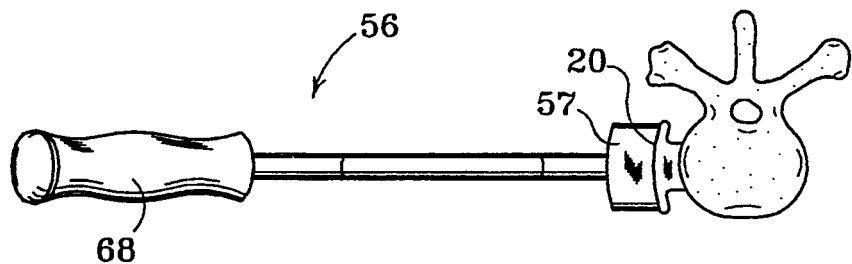
FIG. 7 is a view generally parallel to the spinal column and showing the impactor tool located on the staple as while the staple prongs are being driven into the bone.
Figure 8:
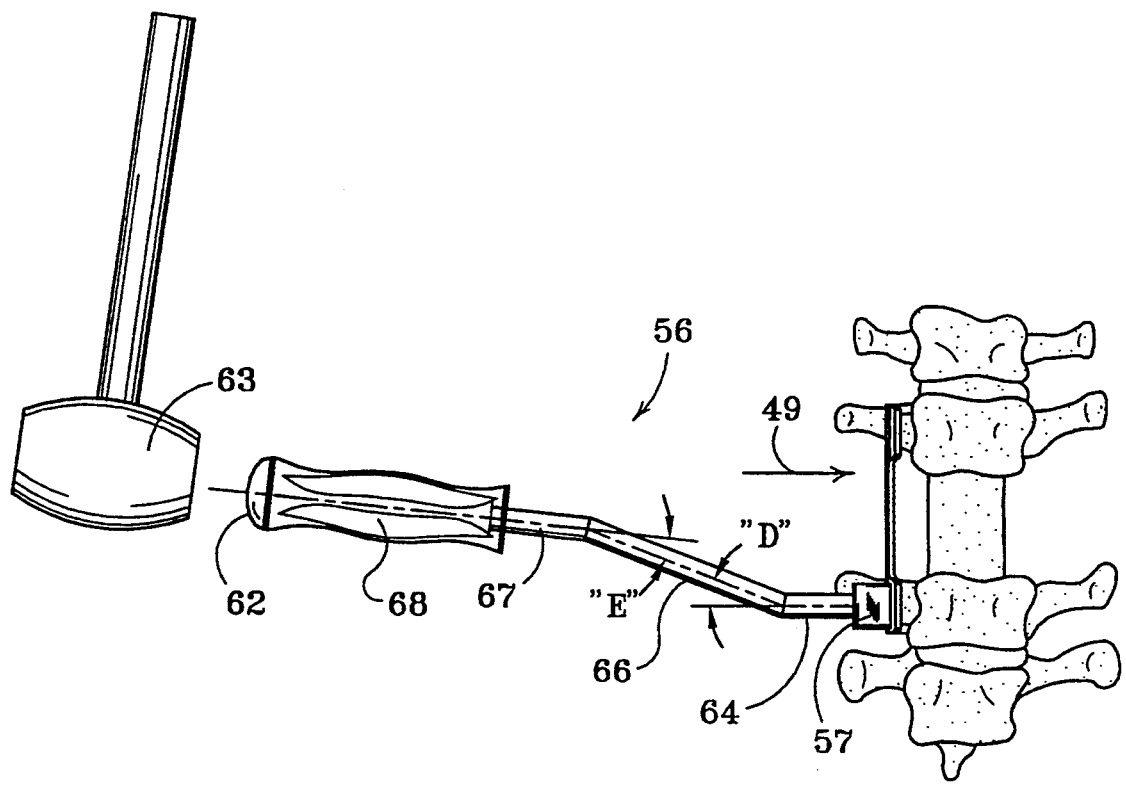
FIG. 8 is a view in a direction transverse to that of FIG. 7 and showing the use of a mallet with the impactor tool.
Figure 9:
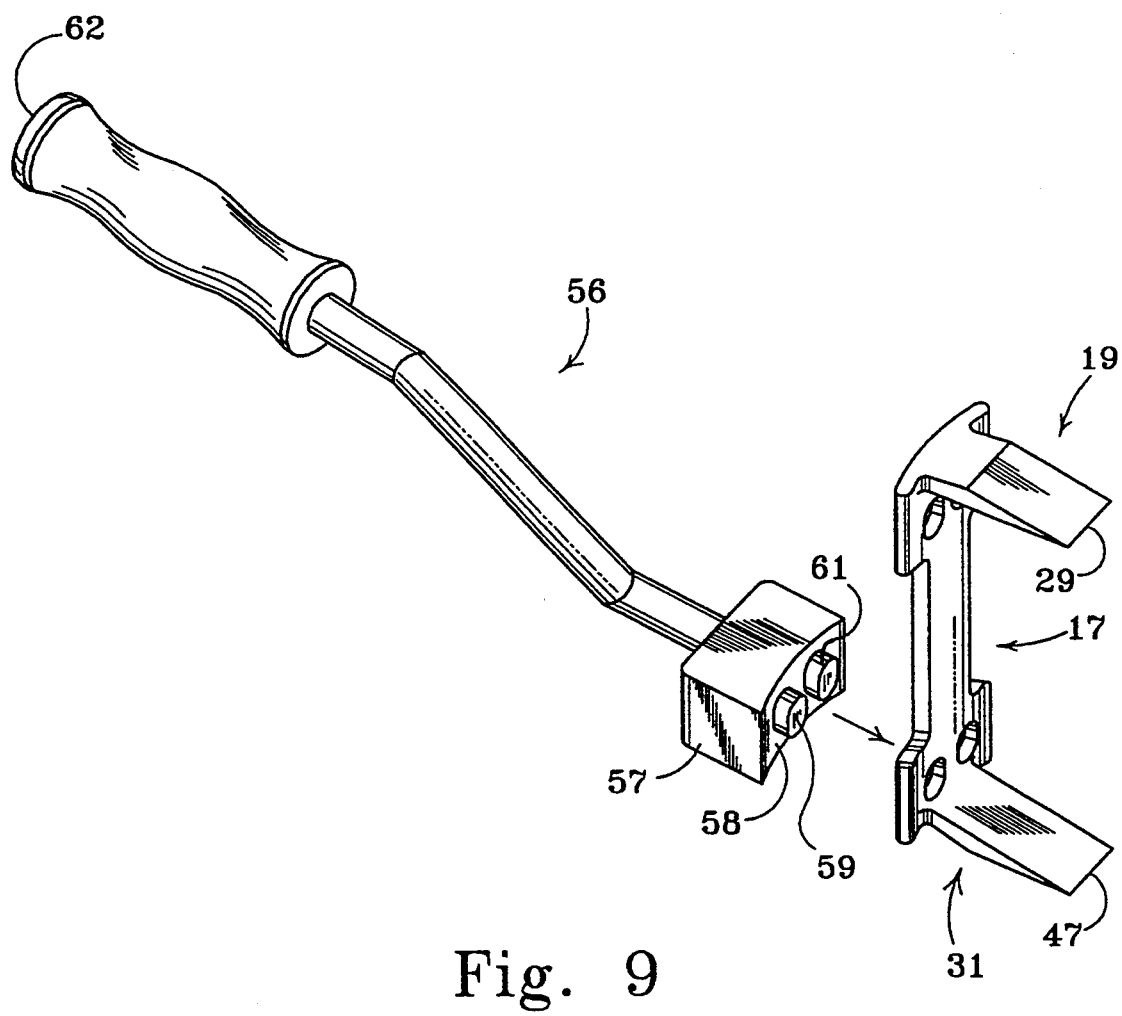
FIG. 9 is a pictorial view of the relationship of the impactor tool to the tool post receiving apertures in the lower end of the staple prior to installing the impactor into the staple for driving the staple.

In the use of the staple, when the desired position of the strut graft bone 14 and the adjacent vertebral bodies 12 and 13, and the abutting surfaces 41 and 42 at the body 12, and 43 and 44 at the body 13 have been established, the sharp edges 29 at the top and 47 at the bottom of the plate are placed on the body 12 and 13, respectively, and driven into the respective body, a little bit at a time at each end. The impactor of FIGS. 7, 8 and 9 is used. During this process, since the inner face 22 of prong 19 is converging with respect to the inner face 48 of prong 31, the bodies 12 and 13 are urged toward each other during installation of the plate in the direction of arrow 49. Accordingly, the strut graft is placed in compression. After the staple has been installed with the prongs at a sufficient depth to be reasonably secure, then the bone screws 49, 51, 52 and 53 are installed.

The impactor 56 includes the mating head 57 having a concave face 58 of a curvature matching that of the convex face 20 of the staple. The head has a pair of posts 59 and 61 which are spaced and sized to be fittingly received in the screw holes in each end of the staple so as to be snugly received therein so that, as the surgeon strikes the handle end 62 of the impactor shaft with the mallet 63, the impactor head will remain in position against the plate. The length of the impactor from head face 58 to handle end 62 is about eleven inches. The height of the posts is about 0.012 inches less than the thickness of the staple plate. The angle "D" between the impactor shaft portion 64 and portion 66 is about 25°. The angle "E" between shaft portion 66 and shaft portion 67 which extends into the grip 68 is about 15°. The material of the impactor head 57 is preferably Teflon brand polytetrafluroethylene material.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A staple for holding in compression a strut graft between two vertebral bodies and comprising:
    an elongate plate having a concavo-convex cross section, with an outer convex face and an inner concave face;
    at least two prongs, each prong having an inboard surface and an outboard surface, the inboard surface of each prong facing the inboard surface of the other prong, the outboard surface of each prong having a proximal portion beginning at the plate and extending outward from the plate, and the outboard surface of each prong having a distal portion beginning at a point on the proximal portion that is remote from the plate and extending outward from that point to meet the inboard surface along a distal edge, the proximal portion of one prong being located at one end of the plate and the proximal portion of the other prong being located the other end of the plate;
    the inboard surfaces of the prongs converging toward each other as they extend from the distal edges of the prongs inward toward the concave face of the plate and converge toward a point in space remote from the convex surface of the plate, there being an angle between lines from the said point in space to the two prong inboard surfaces.

2. The staple of claim 1 and wherein the angle is between four and fourteen degrees.

3. The staple of claim 1 and wherein:
    the inboard surface of each prong extends at an angle from the proximal end of the prong to the distal edge of the prong and which is between five degrees to nine degrees from a line normal to the concave face of the plate.

4. The staple of claim 1 and wherein:
    each prong has the proximal portion of the outboard surface of the prong flat and parallel to the inboard surface, and has the distal portion flat and converging from the proximal portion to intersection with the inboard surface providing a sharp edge at the distal end of the prong.

5. The staple of claim 4 and wherein:
    the proximal portion of the prong is half as wide as the plate at the end of the plate.

6. The staple of claim 1 and wherein:
    the prongs and plate are formed of one homogeneous piece of material and the prongs are at the ends of the plate.

7. The staple of claim 6 and wherein:
    elongate apertures are provided adjacent the ends of the plate,
    there being two apertures adjacent one end, and two apertures adjacent the other end, the apertures being on opposite sides of an elongate central axis of the plate.

8. The staple of claim 7 and wherein:
    the apertures have axes which, at each end, converge toward a point which is at the center of curvature of the concave face of the plate.

9. The staple of claim 6 and wherein:
    the material is titanium alloy suitable for imaging purposes.

10. The staple of claim 9 and wherein:
    the material is titanium 6AL-4V alloy.

11. A method of installation of the staple of claim 7 on a spinal column and comprising the steps of:

installing first on the plate adjacent one end thereof, the head of an impactor tool; and hammering the plate in a direction driving the prong at that end of the plate into a vertebral body of the spinal column.

12. The method of claim 11 and further comprising the step of:

installing on the plate adjacent the other end thereof, the head of an impactor tool; and hammering the plate in a direction driving into another vertebral body of the spinal column, the prong on the other end of the plate.

13. The method of claim 12 and further comprising the step of:

finally anchoring the plate to the vertebral bodies by installing bone screws through apertures in the plate and into the vertebral bodies.

14. The method of claim 12 and further comprising the step of:

locating a concave face of the impactor tool head in a mating relationship to the convex face of the plate as the head is installed on the plate.

15. The method of claim 14 and further comprising the step of:

locating posts on the head of the impactor tool in apertures in the plate as the concave face of the impactor tool is located on the convex face of the plate.

16. The method of claim 15 and further comprising the step of:

holding the posts of the impactor tool in the apertures during the hammering.

17. The method of claim 12 and wherein:

the steps of driving the prongs urge the vertebral bodies toward each other.

* * * * *